(12) United States Patent
Farris et al.

(10) Patent No.: US 8,890,703 B2
(45) Date of Patent: Nov. 18, 2014

(54) PASSIVE WATER HEATER ANODE ROD DEPLETION SENSOR ALGORITHM

(71) Applicant: General Electric Company, Schenectady, NY (US)

(72) Inventors: Brett Alan Farris, Louisville, KY (US); Michelle Diana Gross, Louisville, KY (US); Jonathan D. Nelson, Louisville, KY (US)

(73) Assignee: General Electric Company, Schenectady, NY (US)

( * ) Notice: Subject to any disclaimer, the term of this patent is extended or adjusted under 35 U.S.C. 154(b) by 23 days.

(21) Appl. No.: 13/760,353

(22) Filed: Feb. 6, 2013

(65) Prior Publication Data

US 2014/0216945 A1 Aug. 7, 2014

(51) Int. Cl.
*G08B 21/00* (2006.01)
*C23F 13/00* (2006.01)

(52) U.S. Cl.
CPC .................................. *C23F 13/005* (2013.01)
USPC .................. 340/640; 340/636.12; 340/815.45

(58) Field of Classification Search
USPC .......... 340/640, 636.12, 636.17, 539.27, 514, 340/506–507, 527, 571, 618, 680, 692, 340/3.62, 825.36, 7.61–7.62, 815.45
See application file for complete search history.

(56) References Cited

U.S. PATENT DOCUMENTS

| 2001/0032475 | A1* | 10/2001 | Chen et al. | 62/238.7 |
|---|---|---|---|---|
| 2004/0051514 | A1* | 3/2004 | Kean et al. | 324/71.1 |
| 2007/0179678 | A1* | 8/2007 | Nordberg et al. | 700/300 |
| 2008/0087009 | A1* | 4/2008 | Nishina et al. | 60/301 |
| 2010/0141422 | A1* | 6/2010 | Feinleib et al. | 340/539.1 |
| 2013/0092103 | A1* | 4/2013 | Strand | 122/14.22 |
| 2014/0000729 | A1* | 1/2014 | Meyer | 137/487.5 |

FOREIGN PATENT DOCUMENTS

| CN | 2793637 Y | 7/2006 |
|---|---|---|
| CN | 201837049 U | 5/2011 |
| TW | 200933102 A | 8/2009 |
| WO | WO 2007/010335 A2 | 1/2007 |

* cited by examiner

*Primary Examiner* — Daniel Previl
(74) *Attorney, Agent, or Firm* — Dority & Manning, P.A.

(57) ABSTRACT

The present subject matter relates to methodologies and algorithms for providing anode rod depletion detection and warnings thereof to consumers. Consumers general are not concerned with monitoring consumption of protective anode rods incorporated within water heaters, The present subject matter provides automatic monitoring of anode rod depletion and provides the consumer with notification of rod depletion beyond a predetermined amount by one or more of optical, audible, or electronic devices. Aspects of the algorithm include handling of start-up conditions, service board replacement conditions, and properly defining the anode rod depletion threshold. Additional algorithm aspects include considerations for taking into consideration power outage conditions and accurately estimating galvanic current.

19 Claims, 6 Drawing Sheets

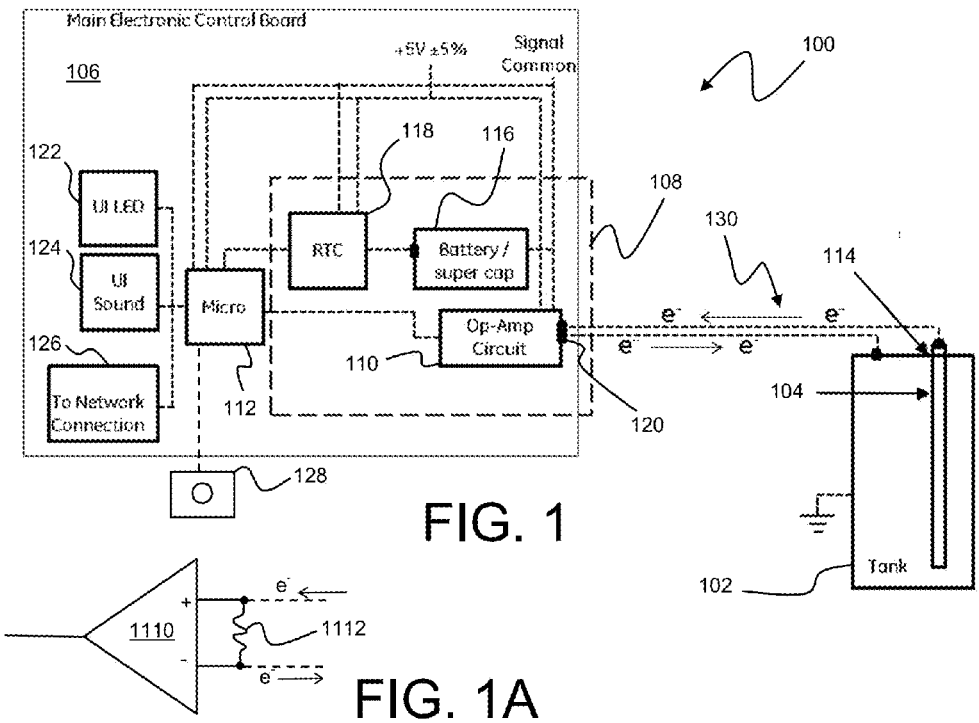
FIG. 1
FIG. 1A
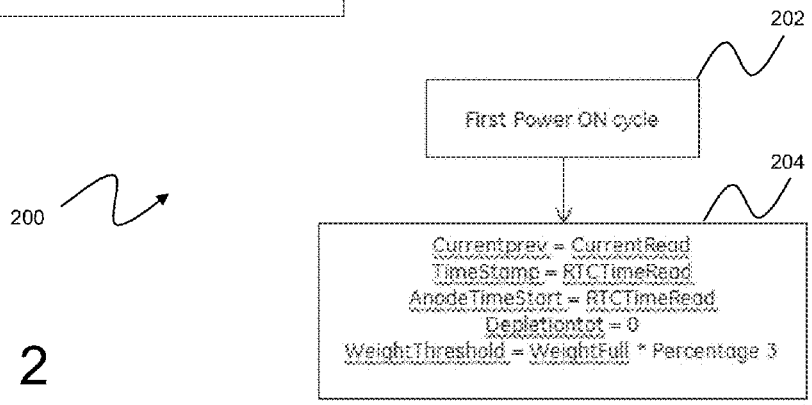
FIG. 2

PASSIVE WATER HEATER ANODE ROD DEPLETION SENSOR ALGORITHM

CROSS REFERENCE TO RELATED APPLICATIONS

The present subject matter is related to U.S. application Ser.No. 13/760,321 entitled "Anode Depletion Sensor Hardware Circuit" filed concurrently herewith, assigned to the owner of the present subject matter, and incorporated herein for all purposes.

FIELD OF THE INVENTION

The present subject matter relates to appliance protection functionality. More specifically, the present subject matter relates to methods and systems for providing various anode rod depletion operational functionalities for water heaters.

BACKGROUND OF THE INVENTION

Passive anode rods are a vital component to water heaters utilizing a steel tank. This sacrificial anode rod provides protection against tank corrosion through galvanic corrosion. The anode rod creates a galvanic current following between the anode and the cathode (the water heater tank) which it is electrically connected. The depletion of the anode rod caused by this galvanic circuit can be calculated by measuring this electric current value and knowledge of the anode rod properties. The measurement circuit components and algorithm used to measure the depletion of a water heater anode rod must be carefully selected to minimized introduced error. This paper describes the circuit and system tolerance stack-up to achieve accurate measurement of the anode rod depletion status.

BRIEF DESCRIPTION OF THE INVENTION

Aspects and advantages of the invention will be set forth in part in the following description, or may be apparent from the description, or may be learned through practice of the invention.

The present subject matter relates to methods for alerting a consumer of water heater anode rod depletion. According to such methods anode rod current flow is periodically measure while at the same time obtain a time reading. Calculations of anode rod depletion are made based on the measured anode rod current and the time difference between the current measurement and the most recent previous measurement. The method then provides for activating an alarm if the calculated anode rod depletion exceeds a predetermined amount.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 provides a block diagram of an anode protection system in accordance with the present subject matter;

FIG. 1A illustrates an exemplary operational amplifier and shunt resistor circuit usable with the system of FIG. 1;

FIG. 2 provides a flow chart of an exemplary anode depletion startup algorithm in accordance with the present subject matter;

Figure 3:
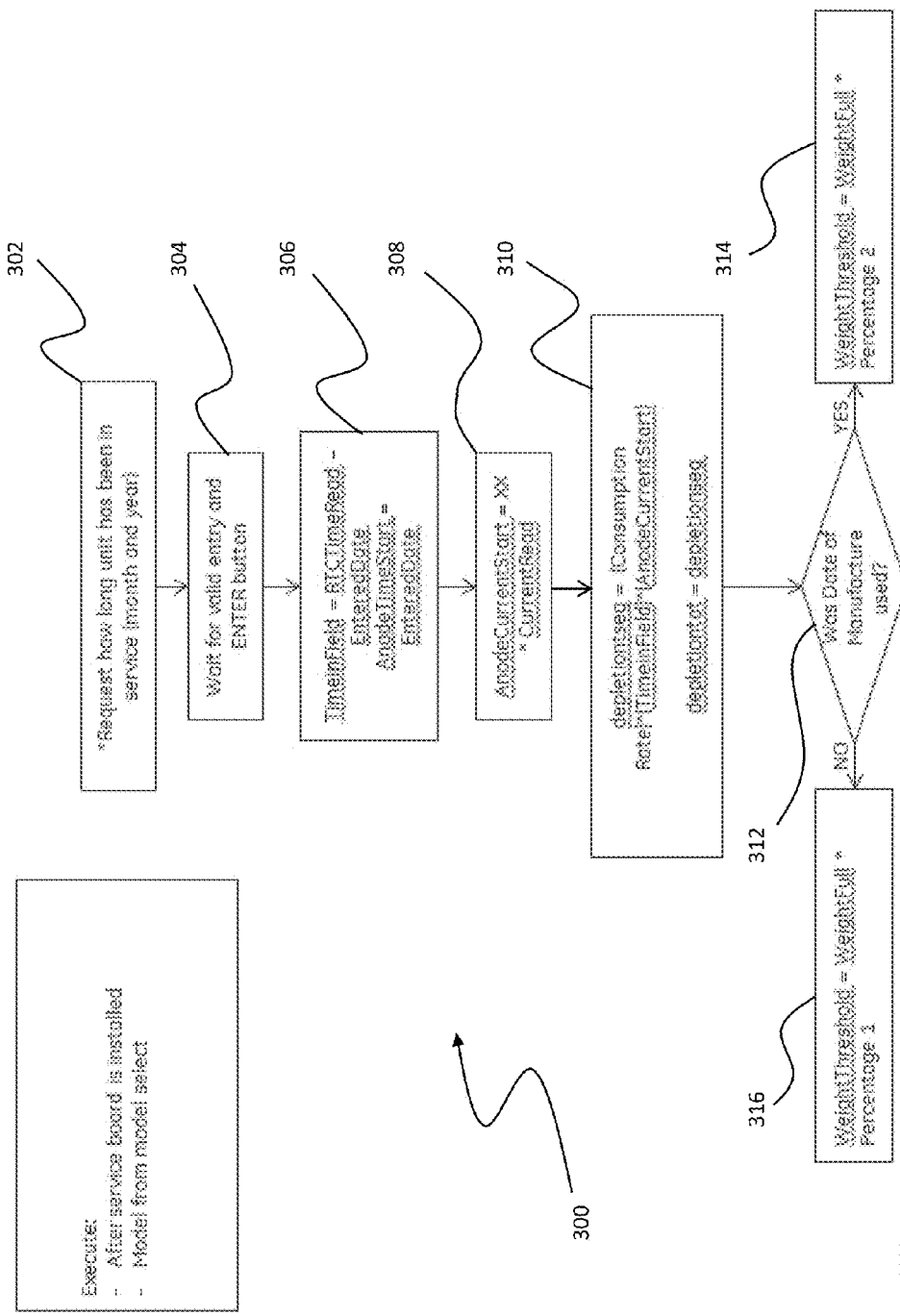
FIG. 3 provides a flow chart of a service board replacement algorithm.

Repeat use of reference characters throughout the present specification and appended drawings is intended to represent same or analogous features or elements.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As previously noted, the present subject matter relates to methods and systems for providing various operational functionalities relating to anode rod depletion for water heaters. With present reference to FIG. 1 there is illustrated a block diagram of an anode protection system 100 in accordance with the present subject matter. Anode protection system 100 corresponds to two major components including a water heater 102 together with its internally mounted anode rod 104 and a main electronics control board 106 including, among other sub-components, anode depletion circuit 108.

In this configuration a passive anode rod 104 is connected to the steel tank of water heater 102 through an anode depletion circuit 108. A galvanic circuit is formed from the connection to the steel tank in which anode rod 104 depletes preferentially to the steel tank.

Using Faraday's Laws of Electrolysis a calculation can be made by measuring the current over time created by the electrons moving from the anode (anode rod 104) to the cathode (the steel tank of water heater 102). The current flow can be calculated using Equation 1 below wherein the specific anode rod material properties and a measurement of the anode rod mass is removed.

$$m = \left(\frac{Q}{F}\right)\left(\frac{M}{z}\right) \times \mathit{Eff} \qquad \text{Eq. 1}$$

Wherein:
m=mass of material removed due to electrolysis
Q=total electric charge passed through the material $$P - 96,480 \frac{C}{\text{mol}},$$

Faraday's Constant
M=molar mass of the material
z=electrons in each ton transfer
Eff=Anode Rod efficiency value In order to measure Q, a modification must be made to the anode-cathode electrical connection as illustrated in FIG. 1. The circuit configuration causes the anode rod 104 electrons (current) to travel through a current sense resistor 1112 as illustrated in FIG. 1A as part of the Operational Amplifier (op-amp) Circuit 110, further illustrated as op-amp 1110 of FIG. 1A. In order to measure this current flow, anode rod 104 must be isolated from the water heater tank at its mounting location, for example by use of isolating insulation, indicated on FIG. 1 as Insulated Cap 114.

In an exemplary embodiment, main electronic control board 106 comprises microcontroller 112, power supply 116, current measurement operational amplifier 110, clock 118 (or other means of retrieving accurate time such as via an Internet clock accessed through network connection 126), and various connections to the water heater anode rod representatively illustrated as connector 120.

Microcontroller 112 receives inputs from operational amplifier 110 and real time clock 118. It should be appreciated that microcontroller 112 may correspond to other types of controllers including a microprocessor or other specially designed hardware and thus the designation as a microcontroller should be broadly interpreted. Microcontroller 112 is configured to perform calculations and make decisions based on operational functionalities and anode rod depletion algorithms as more fully described herein after, and to then provide consumer feedback by way of one or more of a User Interface (UI) display 122, UI sound producing device 124, or by way of connected home appliance communication by network connection 126.

In an exemplary embodiments usable with the functionalities and algorithms of the present subject matter, op-amp circuit 110 incorporates a current sensing resistor 1112 (FIG. 1A) and operational amplifier 1110 to amplify a voltage produced across the current sensing resistor 1112 by current flow in the anode-cathode path generally illustrated as path 130. In an exemplary configuration, such amplified voltage may provide a 0-5V signal corresponding to a gain of 50V/V. In this way the current sensing resistor may correspond to a very small resistive value, for example, about 1.91Ω, and thereby minimize interference to the galvanic current flow of the system.

Those of ordinary skill in the art will appreciate that although the use of a small resistance is advantageous for the galvanic circuit such use generally requires the use of a more precise op-amp circuit. Alternative configuration can be employed, however, by using a corrosion probe such as a silver-chloride probe that generates a voltage corresponding to the level of protection provided by the anode rod. As is understood by those of ordinary skill in the art, a voltage of a specific level or higher is an indication that the tank is being protected by the galvanic circuit. As the current sensing resistor value is increase the voltage reading will decrease and thereby a suitable resistor value can be chosen.

Clock 118 provides an accurate time stamp for the microcontroller when requested by, for example, an operational algorithm. In an exemplary embodiment, clock 118 may correspond to a real-time clock (RTC) 118 and may be powered by battery 116 so that the correct time is maintained. In alternative configurations battery functionality may be provided by a super capacitor. In further alternative embodiments, a thermal energy harvesting circuit can be implemented to provide sufficient energy to keep RTC 118 powered during periods when power is removed from the water heater. A thermal energy harvesting method can utilize the heat from an electric water heater tank or the ignition/main flame from a gas water heater to provide power to the circuit. In alternative embodiments a super capacitor's ability to recharge when external power is available to the control board is advantageous over use of a standard battery. It should also be appreciated that a rechargeable battery may also be employed in a manner similar to rechargeable super capacitors.

Microcontroller 112, like other control boards serves to receive inputs, in this case, from the op-amp circuit 110 and RTC 118 and perform operations. As will be explained more fully later with respect to certain portions of the algorithm described herein, a user accessible panel 128 may also be provided that provides additional input capabilities for microcontroller 112, including, without limitation, a reset button, a alarm silence button, and options for entering data for use by microcontroller 112 in conjunction with the presently described algorithm.

It should be appreciated that the present subject matter is directed more specifically operational functionalities and algorithms for operating systems and sensor circuits configured to provide an indication of anode rod depletion to a consumer. In that regard, the particular circuitry described herein is not a part of the present subject matter but generally it will be understood that the algorithms of the present subject matter are designed to evaluate the condition of anode 104 so as to determine its state of depletion while at the same time minimizing errors as well as minimizing false negative and false positive detection of a depleted anode. An exemplary specific sensor circuit that may be incorporated with the present subject matter has been described in the previously mentioned related US patent application based on U.S. application Ser. No. 13/760,321 entitled "Anode Depletion Sensor Hardware Circuit" filed concurrently herewith, assigned to the owner of the present subject matter, and incorporated herein for all purposes.

In accordance with the present subject matter, there is proved a system controlling operational methodology (algorithm) that may be considered to correspond to six sections. The algorithm chiefly handles the current measurement and depletion summary task, but must also handles power cycles, water heater start-up, control board replacement, anode replacement, and faults relating to the anode rod system.

With present reference to FIG. 2, there is provided a chart 200 of an exemplary anode depletion startup algorithm in accordance with the present subject matter. The water heater startup algorithm 200 portion of the present algorithm executes at the first time the water heater is powered after an End of Line test at the factory. Following startup, that is, first power on, at step 202, algorithm 200, at step 204, takes an initial time stamp and current measurement. It also zeros out the depletion status and sets the warning threshold to a defined percentage of the original anode weight. Step 204 is important due to the time between manufacturing and installation, given that such time frame is a complete unknown. Removing this unknown time variable allows more accurate depletion status estimates to be achieved.

In the event that the control board, for example, main electronic control board 106 (FIG. 1), is replaced after the water heater has been in operation, the exemplary service control board replacement algorithm 300 illustrated in FIG. 3 insures minimal error in the depletion status. It is important that algorithm 300 be run at the time of the control board replacement as, otherwise, nothing will be known about the depletion status of the anode rod.

In accordance with this aspect of the algorithm of the present subject matter, at step 302, a request for time in service information of the water heater will be made and then algorithm will then wait at step 304 for a response. In accordance with the present subject matter, such response may be given from different sources, including, without limitation, a record indicating when the last anode was replace, the date of installation of the water heater, information of a plumber applied sticker if available, or reference to a data of manufacture of the water heater. In certain embodiments of the present subject matter, such information may be supplied from, for example, a flash drive coupled to microcontroller 112 (FIG. 1) or received from the manufacturer or other information source following a request transmitted through network connection 126.

Upon receipt of the appropriate information at step 306, the algorithm will direct, at step 308, that a reading of anode current be taken, and, considering the service time entered, the algorithm will estimate, at step 310, the depletion status of the anode at the time the service board begins operating. Beginning at step 312, the algorithm then determines an appropriate warning threshold for the anode rod. If it is undetermined whether the anode has ever been replaced or if the date of manufacture is used, the warning threshold can be set at step 314 to a defined percentage of the original weight. If the service time is determined by another means then the warning threshold can be set at step 316 to a second, lower, defined percentage of the original weight. The lowered warning threshold is a means to protect against the increased error that could occur due to uncertainty of time in service. Setting to a lower threshold under these circumstances helps to prevent a false positive in the event that the anode rod is depleted or nearly depleted.

Figure 4:
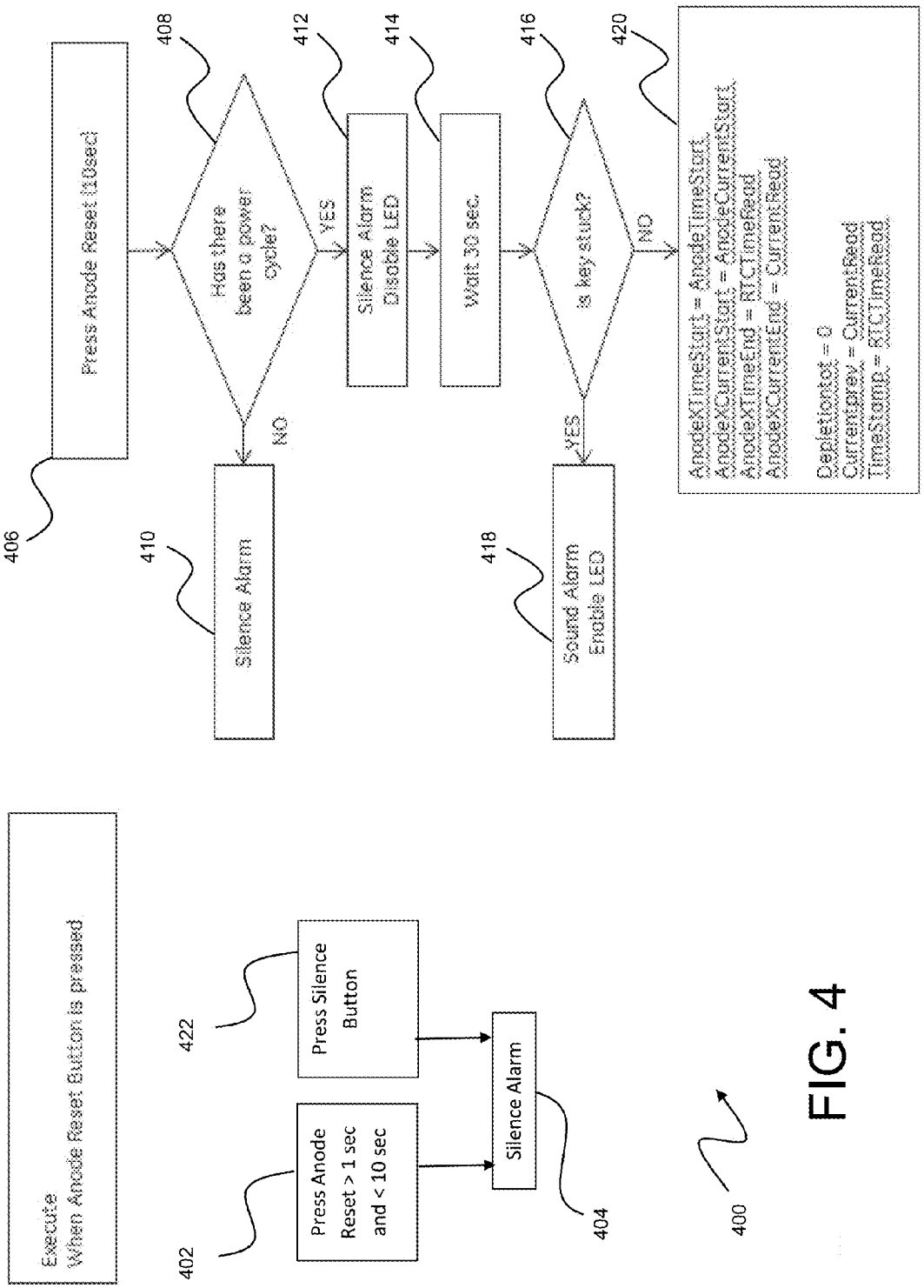
FIG. 4 provides a flow chart of an anode replacement algorithm in accordance with the present subject matter.

With present reference to FIG. 4, a portion of the algorithm directed to anode rod replacement and circuit reset will now be described. Providing the consumer access to an anode rod reset button, for example, a button mounted on user accessible panel 128 of FIG. 1, entails several challenges. The purpose of the anode reset button is to notify the microcontroller 112 that the anode rod has been replaced with a new anode rod. As illustrated in FIG. 4, if an alarm is sounding and the reset button is pressed for less than 10 seconds (step 402) the alarm will silence (step 404) for a predetermined time. In an alternative configuration, a separate alarm silence button may also be provided on user accessible panel 128 that, when pressed (step 422), would immediately silence the alarm. As it is possible that such an alarm can be an urgent alarm the alarm will then sound again after a predetermined time. In an exemplary embodiment, such predetermined time may correspond to 48 hours. If, on the other hand, the button is pressed for more than 10 seconds (step 406) the control will attempt to silence the alarm (step 410) and reset the anode measurement and summation algorithm. First, however, the control will complete verification that power has been cycled recently (step 408) to protect against false reset commands. If this is verified, than at step 420 the previous anode information will be logged, the depletion status will be reset to 0% depletion and an initial current and time stamp reading will be made. In alternative embodiments, however, before resetting the measurement and summation algorithm the control will wait (step 414) to determine at step 416 if this is a stuck key (button) condition falsely triggering the anode reset algorithm. If a stuck key is detected, as alarm may be sounded and an LED enable at step 418 to alert the consumer to the stuck key problem. Those of ordinary skill in the art will appreciate that the 10 second time line for alarm silencing and reset is exemplary and could be change to any convenient time value.

Figure 5:
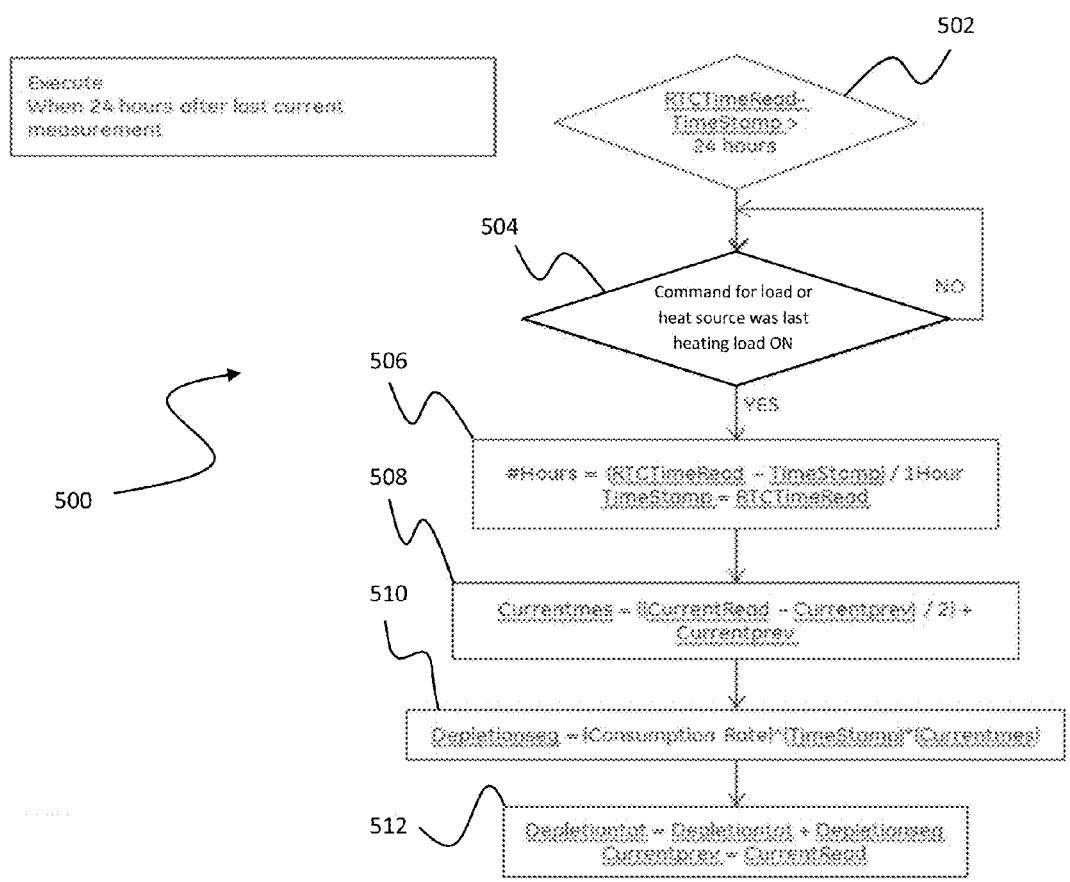
FIG. 5 provides a flow chart of a measurement and summation algorithm used to track anode depletion status in accordance with the present subject matter.

With present reference to FIG. 5, there is provided a flow chart of a measurement and summation algorithm 500 used to track anode depletion status in accordance with the present subject matter. Once the Startup or Service board algorithm has completed this main portion of the algorithm will run to measure and track the anode rod depletion status. Algorithm 500 will execute periodically, for example in an exemplary embodiment, every 24 hours as determined in step 502 after the previous reading. This reading cycle is considered a segment. A reading includes reading (measuring) the anode rod current and real time clock (RTC). It should be appreciated that while a 24 hour time frame is exemplary for the present subject matter, the longer a segment is, the more error that can accumulate over that time, thus shorter periods, for example, one hour time frames may be employed. Error accumulates because an interpolation is occurring between the previous and present current readings creating an average reading to use in Eq. 1 above. The present algorithm allows the system to handle power OFF conditions by tracking the RTC time by powering the device with a battery 116 (FIG. 1) or other external power independent energy source.

Figure 6:
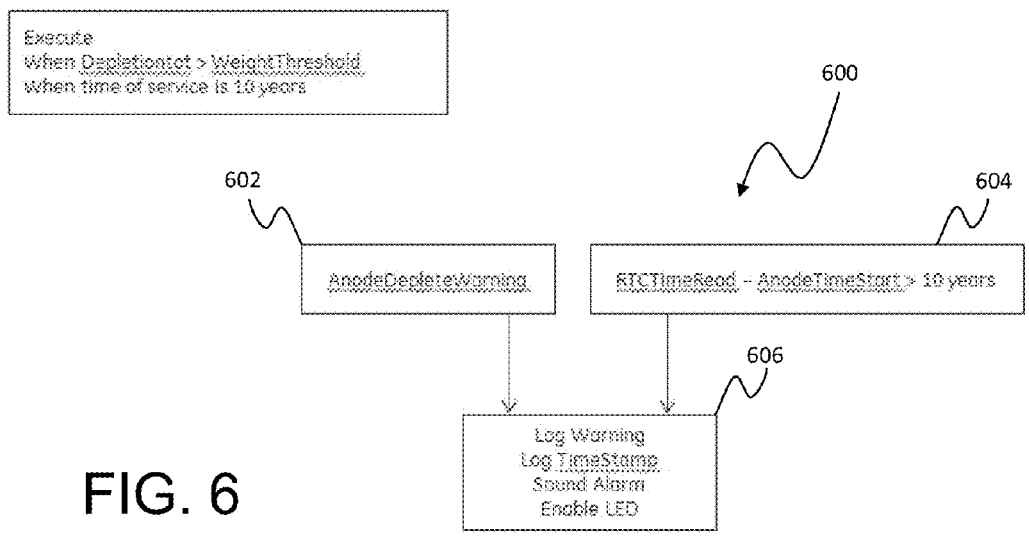
FIG. 6 provides a flow chart of an anode depletion threshold limit algorithm that is executed in accordance with the present subject matter under certain anode weight and service time conditions FIG. 7 provides a flow chart indicating certain anode system fault algorithms.

To take the readings the heating elements cannot have been enabled in the recent past. This is checked as step 504 by waiting for a heating element command or if the heat-pump was the last load ON the control will perform the reading. Once the readings including time readings at step 506 and current measurement at step 508 are complete, calculations are performed at step 510 to determine the depletion of the anode rod over the last time segment, that is, the time period from the current measurement since the most recent previous current measurement. This reading is then summed at step 512 with the previous depletion weight total. Algorithm 500 then prepares for the next cycle by saving the current value to the current previous register. With respect to step 508, it should be noted that the current measurement calculations include an averaging process based on a present current measurement and a previous current measurement. In this way With present reference to FIG. 6, Anode Rod Depletion Threshold Limit Algorithm 600 is configured to execute in the event that the depletion status total is greater than the defined weight threshold (step 602) or in the instance that the anode rod has been in service for more than a predetermined period of time, for example, more than 10 years (step 604). Algorithm 600 will log the warning event (step 606) in accordance with a control fault recording procedure and will also log the time stamp for future use. This time stamp allows a service technician or a quality engineer to determine if the weight threshold has ever been reached, when it occurred, and if the anode rod was replaced.

Figure 7:
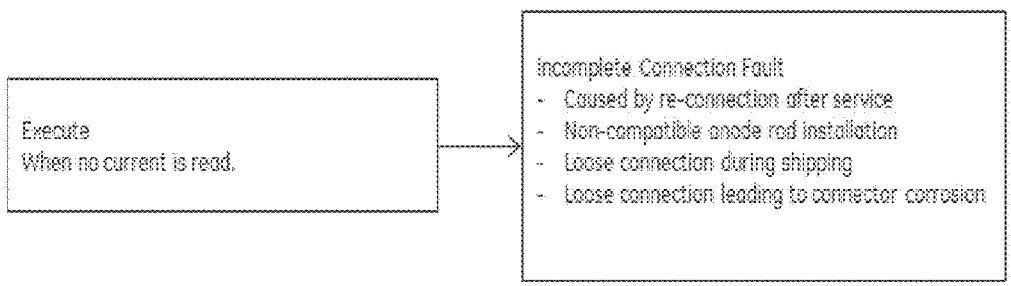

With present reference to FIG. 7, the no current read fault there represented is considered to be an urgent fault. If, after installation of a water heater and application of operating power (electrical connection) or other energy source (e.g., gas) there is no current flow detected in the anode rod circuit, an urgent fault requiring immediate attention may have occurred. If, for example, there is a loose or broken connection in some extreme instances there can be very little time (for example, about a week) before the steel tank will corrode through and begin to leak. The incomplete connection fault is meant to warn the consumer or service technician that the anode circuit is not connected or has been re-connected incorrectly.

Figure 8:
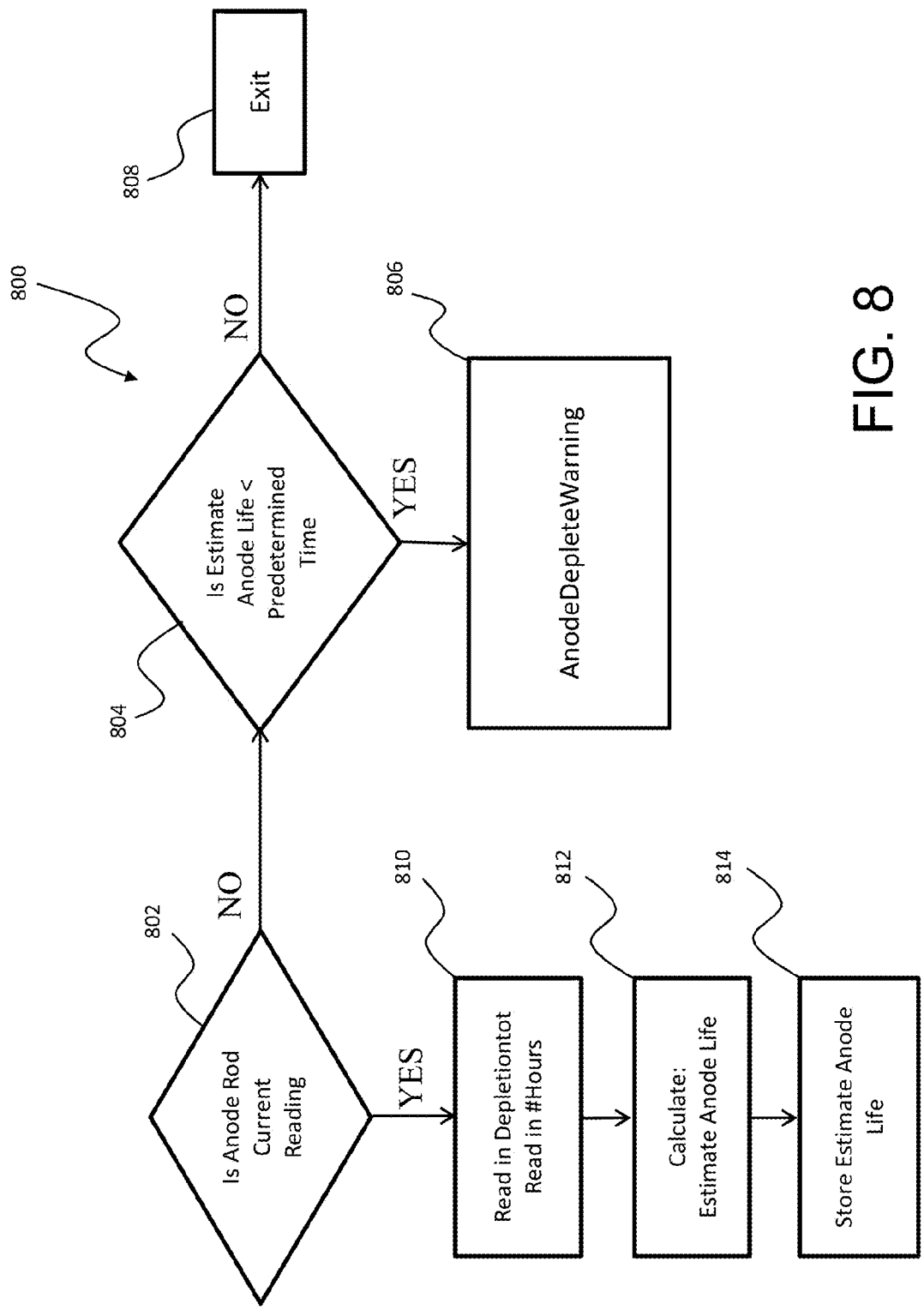
FIG. 8 is a flow chart illustrating an anode rod current reading fail algorithm in accordance with the present subject matter.

With present reference to FIG. 8, there is illustrated a flow chart of an algorithm 800 illustrating anode current read functionality that provides a backup functionality if the anode circuit is damage and not providing an accurate voltage to correlate to current. As illustrated in FIG. 8, algorithm 800 begins at step 802 by determining whether readings are being made of an anode rod current. If not, step 804 determines whether the estimated anode life is less than a predetermined time and, if so, causes an alarm to be given (step 806) and then exits at step 808. If, on the other hand step 802 determines that anode current is being read, readings of anode depletion and time are updated in step 810 and calculations are made in step 812 of estimated anode life that are stored in step 814 for future use. Algorithm 800 is configured to continually updated information until the anode current sensing circuit is not functional.

The algorithm herein described in accordance with the present subject matter, used in combination with anode rod current sensing circuitry, provides detection of anode rod depletion status and significantly improves overall system functionality.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for alerting a consumer of water heater anode rod depletion, comprising:
    initializing anode current readings and time readings to correspond to a current anode rod current and time reading when operating power is first applied to the water heater at initial installation and anode depletion;
    initializing a value of total anode rod depletion to zero; and
    initializing a weight threshold of the full weight of the anode rod to a first predetermined percentage for use in calculating anode rod depletion;
    periodically measuring anode rod current flow;
    obtaining a time reading at the time of current measurement;
    calculating anode rod depletion based on the measured anode rod current and the time difference between the current measurement and a most recent previous measurement; and
    activating an alarm if anode rod depletion exceeds a predetermined amount.

2. A method as in claim 1, wherein the anode rod current is measured based on predetermined measurement periods.

3. A method as in claim 1, wherein calculating anode rod depletion is based on averaged current measurements.

4. A method as in claim 1, wherein obtaining a real time clock reading comprises obtain a reading from an energy source backed up real time clock.

5. A method as in claim 1, further comprising:
    activating an alarm if anode rod usage time exceeds a predetermined time.

6. A method as in claim 1, further comprising:
    delaying anode current measurements until a predetermined time following disablement of water heater heating elements.

7. A method as in claim 1, wherein activating an alarm comprises activating one or more of a visual, audible, and electronic device.

8. A method as in claim 7, wherein the indicator comprises one or more of a light emitting diode (LED) and a sound source.

9. A method as in claim 7, wherein the electronic device comprises a network enabled device,
    whereby indications of anode rod depletion may be sent to a remote location.

10. A method as in claim 9, wherein the time reading is obtained through the network enabled device.

11. A method as in claim 1, further comprising:
    initializing a weight threshold for anode rod depletion calculations based on the length of time the water heater has been in service following field replacement of a water heater service board.

12. A method as in claim 11, wherein the weight threshold is adjusted based on whether a date of manufacture of the water heater is used to determine the water heater length of service.

13. A method as in claim 12, wherein the weight threshold is adjusted to a lower value if the date of manufacture of the water heater is not used to determine the water heater length of service than if the date of installation of the water heater is used to determine the water heater length of service.

14. A method as in claim 1, further comprising:
    deactivating an alarm upon closure of a reset button for less than a predetermined time period or upon activation of an alarm silencing button.

15. A method as in claim 1, further comprising:
    initializing time, anode current, and anode depletion values upon closure of a reset button for more than a predetermined time following field replacement of the anode rod.

16. A method as in claim 15, further comprising:
    evaluating operation of the reset button to determine whether the button is stuck closed before initializing time, anode current, and anode depletion values.

17. A method as in claim 16, wherein evaluating operation of the reset button corresponds to determining whether the button is closed for more than a predetermined time.

18. A method as in claim 1, further comprising:
    storing an estimated anode rod life based at least in part on measured anode current.

19. A method as in claim 18, further comprising:
    issuing an alarm if no value is obtained from a measurement of anode current or the estimated anode life is less than a predetermined time period.

* * * * *